United States Patent [19]

Falk

[11] Patent Number: 4,815,326

[45] Date of Patent: Mar. 28, 1989

[54] OXIDE FREE SAMPLER

[76] Inventor: Richard A. Falk, 122 Nurmi Dr., Ft. Lauderdale, Fla. 33301

[21] Appl. No.: 111,086

[22] Filed: Oct. 19, 1987

Related U.S. Application Data

[63] Continuation of Ser. No. 863,176, May 14, 1986, abandoned.

[51] Int. Cl.⁴ ............................................ G01N 1/12

[52] U.S. Cl. ............................ 73/864.52; 73/864.53; 73/DIG. 9

[58] Field of Search ......... 73/DIG. 9, 864.51, 864.52, 73/864.53, 864.54, 864.82, 863.21

[56] References Cited

U.S. PATENT DOCUMENTS

| | | | |
|---|---|---|---|
| 2,515,060 | 7/1950 | Smith | 73/DIG. 9 |
| 3,354,723 | 11/1967 | Smith | 73/864.54 |
| 3,452,602 | 7/1969 | Hackett | 73/DIG. 9 |
| 3,460,393 | 8/1969 | Putnam | 73/864.54 |
| 3,967,505 | 7/1976 | Feichtinger | 73/DIG. 9 |
| 4,007,641 | 2/1977 | Kelsey | 73/864.54 |
| 4,037,478 | 7/1977 | Cure | 73/DIG. 9 |
| 4,170,139 | 10/1979 | Narita et al. | 73/864.52 |
| 4,445,390 | 5/1984 | Atwell . | |

FOREIGN PATENT DOCUMENTS

| | | | |
|---|---|---|---|
| 1922677 | 5/1969 | Fed. Rep. of Germany . | |
| 39-8648 | 5/1964 | Japan . | |
| 0002358 | 1/1978 | Japan | 73/864.52 |

OTHER PUBLICATIONS

King, "Sampling of Liquid Metal", Determination of Gases in Metals, Special Report No. 68, 3-18 (Iron & Steel Institute), p. 12, 1960.

Automatic Analyzers for Industry Research, Leybold-Heraeus LECO RH-101 & DH-102 Advertisement, Sep. 1983 American Laboratory.

LECO Advertisement "Products for Hydrogen Determination" Automatic Hydrogen Analyzer H2A 3001 with Disposable Suction Sampler ESK System Dr. Feichtinger, Leybold-Heraeus.

"Custom Metal Heat Treating since 1956" Metal-Lab, Inc.

"Archiv fur das Eisenhuttenwesen", Dec. 1970, and translation.

*Primary Examiner*—Stewart J. Levy

*Assistant Examiner*—Robert R. Raevis

*Attorney, Agent, or Firm*—Fuller, Puerner & Hohenfeldt

[57] ABSTRACT

A molten metal sampler which can be pre-evacuated is provided with a double skirt end structure to receive, chill and solidify molten metal around the fill end to reinforce the outer tube and minimize erosion of the outer housing during immersion.

7 Claims, 3 Drawing Sheets

OXIDE FREE SAMPLER

This is a continuation of co-pending application Ser. No. 863,176, filed on May 14, 1986, now abandoned.

FIELD OF THE INVENTION

The invention relates to molten metal sampling devices for retrieving a sample for subsequent analysis.

BACKGROUND OF THE INVENTION

The invention relates to molten metal samplers, particularly adapted for forming a pin sample which can be used in a combustion analyzer or other analysis equipment for determining various properties of the sample, and hence, properties of the molten melt from which the sample is obtained. The molten metal sampler can be pre-evacuated and thus can provide a sample without an oxide coating which avoids the necessity of removing the oxide surface by machining prior to certain types of analysis. The sampler can be sized to interfit in gas analysis equipment such as that manufactured by Leco Corporation and referred to in U.S. Pat. No. 4,445,390.

When used for analysis of hydrogen, the prior art samplers, such as that disclosed in U.S. Pat. No. 4,445,390 and U.S. Pat. No. 3,967,505 employ closure or screen means to separate the inner sample chamber from the outer evacuated chamber or housing and permit gases evolved from the sample chamber during sample rooting to enter the outer chamber but prevent molten metal from entering the outer chamber. The gases evolved during cooling become accessible in the outer chamber or housing for retrieval and analysis. The closure means enables release of all gases including oxygen, nitrogen and hydrogen evolving from the cooling sample. One of the objects of samplers of this category is to provide a good seal at the inlet end of the sample mold as the metal cools to prevent outflow of metal and also seal the evolved gases in the sampler for later analysis. The prior art techniques have not consistently provided good results.

SUMMARY OF THE INVENTION

The sampler of the invention provides a double or concentric metal skirt at the fill end of the sample mold which defines a secondary metal fill cavity which receives an annular ring of molten metal when immersed to preheat all metal parts around the sample mold inlet to facilitate welding of the molten metal to the sampler to seal the sample mold. The secondary metal is chilled and desirably solidified to reinforce the outer housing and limit erosion of the end of the housing during immersion. Welding of the molten metal to seal the sample mold is also facilitated by a metal tapered inlet throat which tapers to an annular knife edge. The thin metal edge increases in temperature rapidly to provide a better weld or fusion with the sample metal in the inlet end as the sampler is withdrawn from the metal bath.

One embodiment of the sampler discloses the use of a fused quartz tube as a sample mold which is sealed at the remote end and open at the inlet end and can have a restriction intermediate the length of the sample mold tube rather than between the sample mold and outer chamber to limit movement of molten metal to define a predetermined length of a pin sample. There is no closure or screen means to permit gases to go into the outer chamber but prevent metal flow as in the prior art patents noted above. Thus, standarized lengths of the pin samples will be formed of approximately the same weight so that the analysis of one pin sample can be correlated with the analysis of other pin samples of similar length. The fused quartz tube is sealed at the remote end and the cooling metal will seal the inlet end and hence all evolved gases will be temporarily trapped in the quartz tube. Diffusible or evolved hydrogen can be accessed for measurement by breaking the internal quartz sample tube while still in place in its outer housing prior to inserting the same in a gas analyzer of the type shown in U.S. Pat. No. 4,445,390. The breaking can be accomplished by striking the exterior housing. The portion of the fused quartz tube between the restriction and the closed end comprises a chamber which, when evacuated, assists in vacuum filling the sample tube.

An important feature of the invention is to provide mounting means for the fused quartz tube which in disclosed embodiments is made of metal and can be machined and shaped to afford certain advantages as noted above to chill the sample and promote a good seal by welding. The mounting means also provides the inner concentric skirt to form the ring of secondary metal.

The mounting means is rigidly secured to the fused quartz tube to provide an integral extension of the tube and form part of the sample mold itself. Samplers made in accordance with the disclosure herein have provided good test results. Further objects, advantages and features of the invention will become apparent from the disclosure.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

Figure 1:
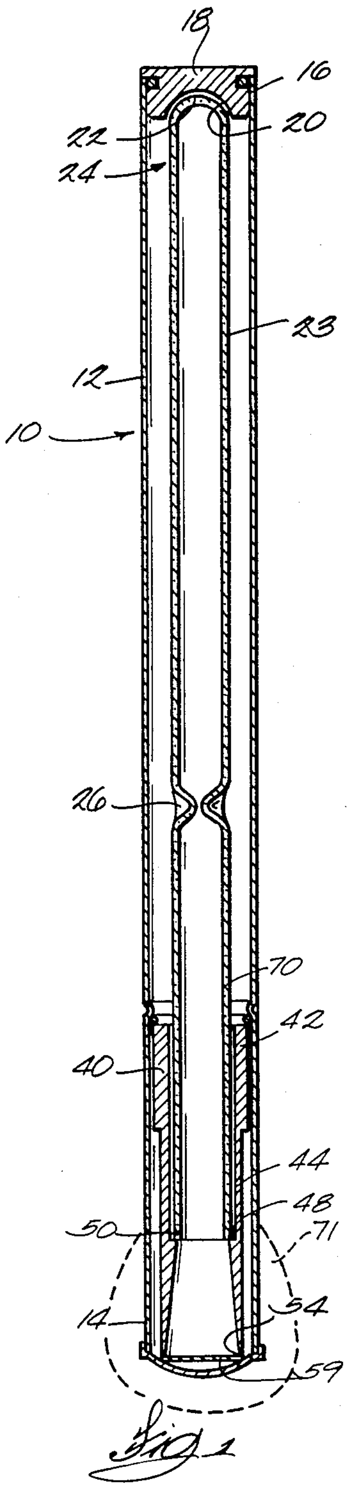
FIG. 1 is a sampler in accordance with the invention in fragmentary section.
Figure 2:
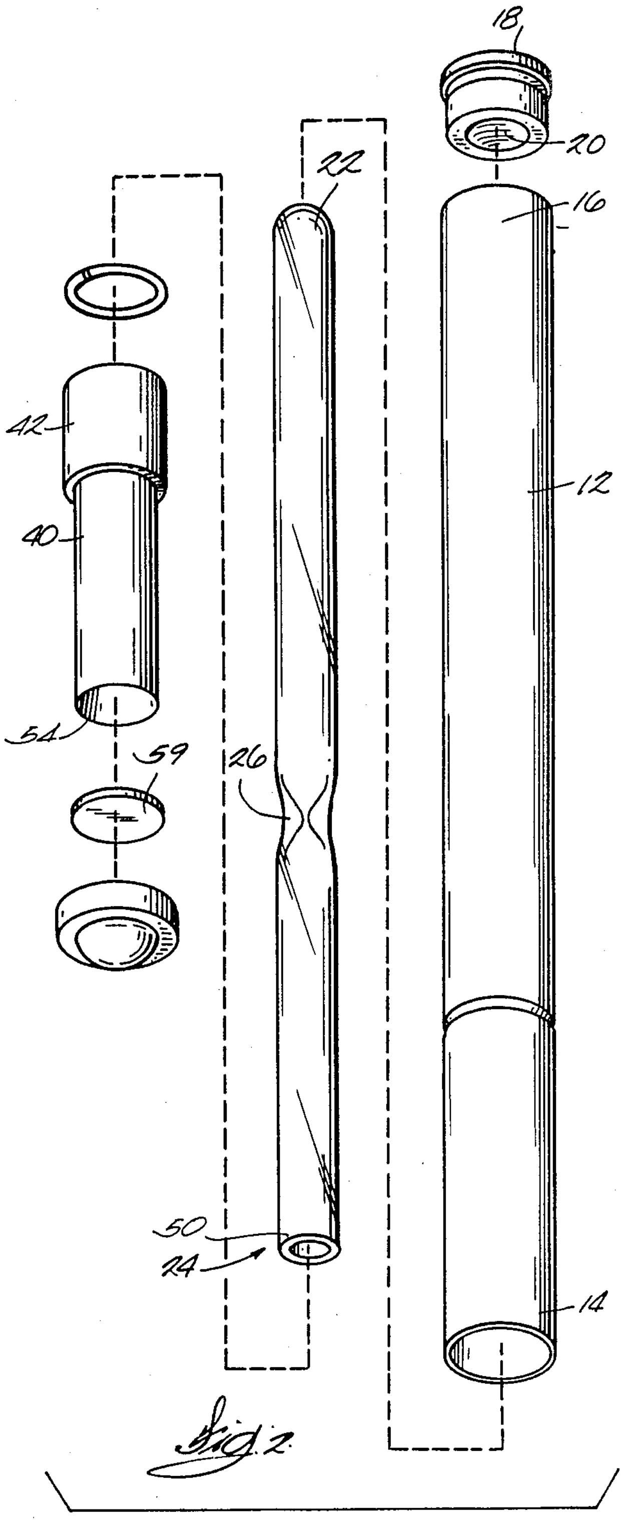
FIG. 2 is an exploded perspective view of the various components of the sampler shown in FIG. 1.

FIG. 1 shows a molten metal sampler 10 which has an outer housing 12 formed from a cylindrical tube which can have a thin metallic wall as illustrated. The tube 12 has a first end 14 and a second end 16. The second end 16 is sealed by a plug means 18 which can be brazed, soldered, cemented or otherwise secured to the outer housing 12. The plug 18 can be provided with a concave recess 20 for receiving the rounded end 22 of a sample mold tube 24. The recess 20 will assist in proper positioning of the tube 24 The recess 20 can be complementary in shape to the end 22.

Figure 6:
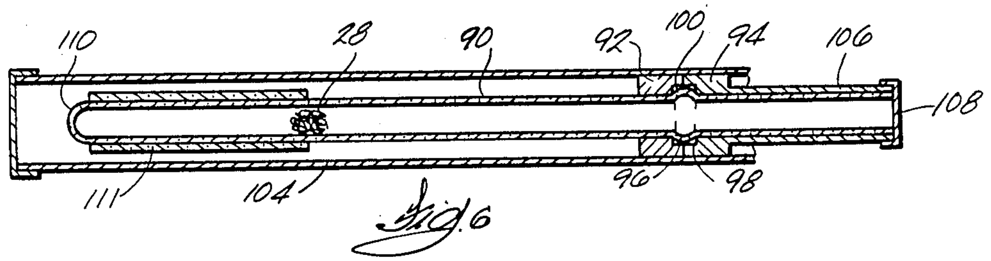
FIG. 6 is a further modified embodiment of the invention.
Figure 10:
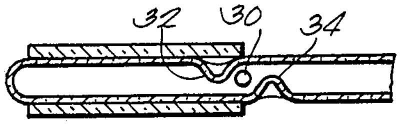
FIG. 10 shows a further variation of the sample mold tube.

The sample mold 24 can have a restriction or constriction means 26 to limit molten metal flow past the constriction so as to provide a pin sample having a predetermined length, the length of tube 70 between 26 and the tip or end 50 is the sample forming portion of the tube 70. In FIG. 1 the constriction is similar to the evacuated tube sampler illustrated on page 266 in the article entitled *Improved Methods of Sampling and Analysing the Hydrogen Content of Molten Steel* in Archiv fur das Eisenhuttenwesen, December, 1970, by Von Theo-Kurt Willmer and Klaus Zimmermann. Other means to limit the length of the pin is shown in FIGS. 6 and 10. In FIG. 6 some metallic wool 28 is cemented or otherwise held in place. In FIG. 10 a bearing ball 30 located and retained between axially spaced protrusions 32 and 34 is employed.

The large vacuum reserve afforded by the relatively long extension 23 of the tube 24 beyond the restriction does cause slivers of molten metal to enter into the extension 23. It is not necessary to employ the restriction for all applications and some samplers have been satisfactorily tested without the restriction.

In accordance with the invention, mounting means are provided to support the sample mold tube 24 in the interior of the housing 12. In the construction disclosed in FIG. 1, the mounting means comprises a sleeve 40 which is shown in enlarged detail in FIG. 3. The sleeve 40 has a portion 42 integral with a portion 44 having a diameter less than the portion 42 but located coaxially with a common internal diameter Portion 42 has an outside diameter approximating the inside diameter of the housing 12 to afford a seal with the use of an aluminum oxide or refractory cement or the like at 46 between the housing wall 12 and the outer diameter of portion 42. The mounting means includes a shoulder 48 which can provide a seat for the end 50 of the sample mold. A tapered throat 52 extends from the extreme tip 54 in the form of an annular knife edge. The thin metal around the knife edge more readily increases in temperature that thicker metal and hence can more readily weld or fuse to the sample metal to provide a seal for the sample mold to seal in place evolved gases if evolved gases are to be measured.

Figure 3:
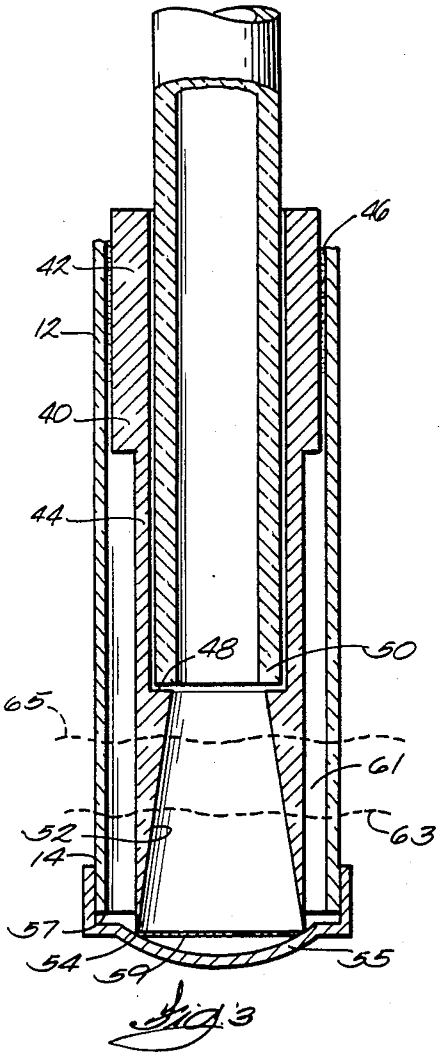
FIG. 3 is an enlarged sectional view of a portion of the sampler shown in FIG. 1.

As best illustrated in FIG. 3, the knife edge 54 of the filling end projects beyond the first end 57 of the tube 12 to minimize sample contamination by molten metal from the end 57 of the housing. In addition, the brazing disk 59 will cause brazing metal to adhere to the knife edge 54 to provide a seal and integrate by brazing the mounting means sleeve 40, the fusible cap 55 and the outer housing 12 to retain the vacuum.

In accordance with the invention, means are provided to provide an annular receptacle 61 surrounding the pip 50 of the sample mold to enhance sealing and reinforce the terminal structure. In the disclosed construction, the means comprises a double skirt or pair of concentric walls which define the annular chamber or receptacle 61. The concentric walls disclosed in FIG. 3 comprise the outer housing wall 12 and the sleeve portion 42, which are concentric and spaced. When the sampler is immersed to retrieve a sample, the molten metal flows into the chamber 61 and is chilled and solidified. This secondary metal thus rigidifies the outer housing wall 12, thus minimizing erosion of this wall adjacent the tip. The result is that the housing 12 will erode off at a more predictable point such as at line 63, rather than closer to the end 50 at line 65. As a result, the plug of metal formed at the end of the sampler will be more uniform and in a predetermined relationship to the sample. This may provide more uniform results in the quantity of evolving gases trapped in the sample mold tube. There is some belief that gases such as hydrogen which are released as the sample cools, can be transmitted from the outer plug into the cavity of the housing. Hence, hydrogen evolving from the plug shown in dotted lines in FIG. 1 at 71 can end up in the sample cavity and the interior of housing 12 as a result of the vacuum in housing 12. Additionally, a better seal of gases in the sample mold at the inlet is achieved.

The axial extent of the portion 44 and the wall thickness can be varied to provide the desired results in chilling the sampler. The tapered metal throat also provides a chill.

In a sampler successfully tested, the dimensions of the quartz pin was 5×7 millimeters and the length $5\frac{3}{8}$ inches. The entrance sleeve 40 had an outside diameter of 11/32 inches (8.731 mm) and was made from 1045 steel and had a total length of 38.1 mm. The sleeve tapered from 11/32 inches (8.731 mm) to 0.190 inches (4.826 mm) and had a length from the shoulder to the inside end of the sleeve of 1 inch (25.4 mm) and an axial length of $\frac{1}{2}$ inch for the larger diameter portion 42. As illustrated the end 54 projects beyond the end 14 of the fill tube and seals against the cap. The cap and tip can be integrally sealed by a brazing disk 56 which will form an integral sealed assembly at the tip. If it is intended to evacuate the sampler, the brazing would be done in a vacuum oven or the like.

Figure 4:
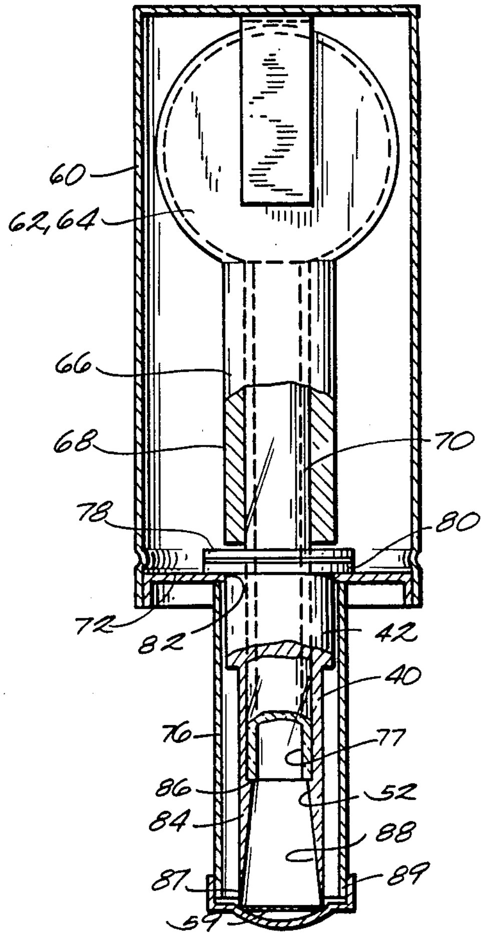
FIG. 4 is an enlarged fragmentary sectional view of a modified embodiment of the sampler.
Figure 5:
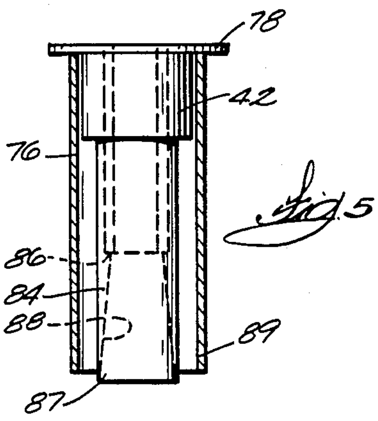
FIG. 5 is an enlarged view of part of the sampler shown in FIG. 4.
Figure 7:
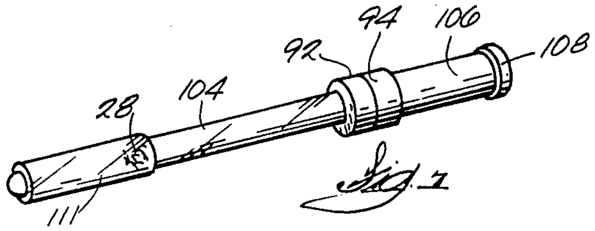
FIG. 7 is a perspective view of a portion of the sampler shown in FIG. 6.

The embodiment shown in FIG. 4 shows a housing 60 which could have a larger diameter to accommodate a split metal mold with clam shell mold halves 62, 64 of the type shown in various of my prior patents such as U.S. Pat. No. 3,905,238. The mold halves would have opposed metal extensions 66, 68 which would receive the end of a fused quartz pin sample tube 70. At the end 72 of the housing 60, a housing portion 76 extends therefrom and is provided with a mounting means which can include a flange portion 78 which seats against mounting means 80 inside the container. Housing 76 extends through an aperture 82 in the end wall. Contained within the housing 76 is an inlet sleeve or mounting means 84 which has an internal shoulder 86 and a tapered throat 88. The fused quartz sample tube 77 can be seated against the shoulder 86. The end 87 projects beyond the end 89 of the second housing as illustrated in FIG. 5. The double skirt provided around the tube 70 provides the annular ring of molten metal which provides the benefits mentioned above.

FIGS. 6, 7, 8 and 9 show modified embodiments of the invention in which the mounting means for a fused quartz tube 90 comprises split blocks 92 and 94 which have recesses 96 and 98 in facing relationship which capture a bulb or annular protrusion 100 on the quartz tube 90. Thus, the quartz tube is positively positioned and supported concentrically within the outer housing 104. Mounting block 94 can be provided with an axial extension 106 and cap 108. The sampler may or may not be evacuated depending on the end use. All the embodiments illustrated can be pre-evacuated and sealed by brazing in a vacuum oven. The extended tube portion between the metal wool 28 and the tip end 110 provides a reservoir to enable compression of air in the fill tube during filling if the fill tube is not pre-evacuated.

Figure 8:
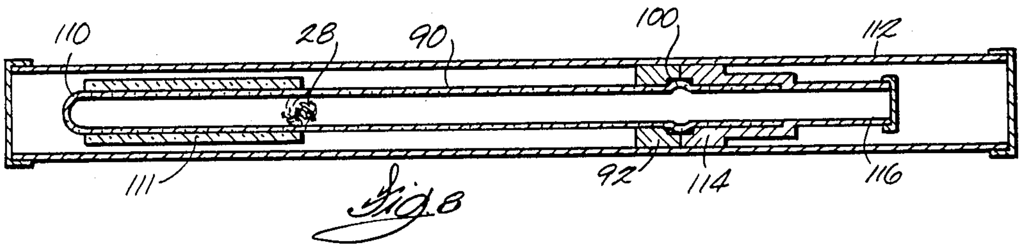
FIG. 8 is a further modified embodiment of the invention.
Figure 9:
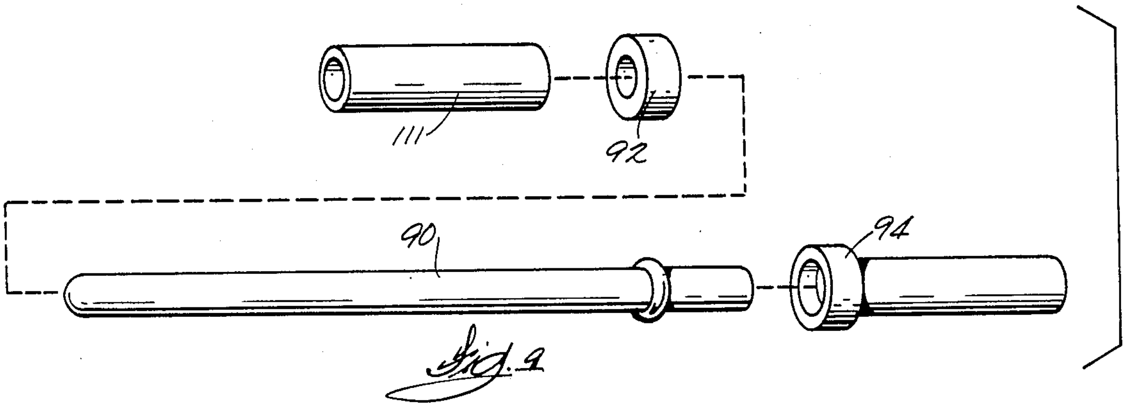
FIG. 9 is a perspective exploded view of the sampler components illustrated in FIG. 6.

FIG. 8 shows a modified embodiment in which the sample mold 90 is located wholly within an outer housing 112 and the mounting means 114 can be provided with a stepped portion 116. The glass or quartz sleeve 111 can be employed to engage the needles which puncture housing 112 to enable breaking of the tube 90 by needle pressure of the needles in a gas analysis of the Leco-type mentioned above.

I claim:

1. A molten metal sampler comprising an evacuated outer housing having a continuous sidewall and first and second ends, a sample mold having a mold sample forming passage and first and second ends, mounting means for supporting said sample mold in said housing, said means including a mounting block having a through aperture, said sample mold being received in said aperture and means to secure said mounting means to said housing and wherein said sample mold comprises a fused quartz tube having first and second ends and said mounting means including an extending portion with an inlet end which extends past said first end of said simple tube and beyond said first end of said housing and said extending portion having a tapered wall forming a tapered aperture in coaxial relationship with said sample forming passage to provide a continuous flow path for entry of molten metal, said tapered wall terminating in a knife edge to promote fusion of said edge with the sample metal to seal gases in said sampler evolving from said sample metal.

2. A molten metal sampler in accordance with claim 1 including a second housing having a larger diameter than said first housing, means for mounting said second housing in coaxial relationship to said first housing and wherein said sample mold extends into a secondary sample mold within said second housing and said sample mold forming a flow passage to afford filling of metal into said secondary sample mold within said second housing.

3. A molten metal sampler of claim 2 wherein said secondary sample mold includes split mold halves and wherein both said first and second housings are pre-evacuated.

4. A molten metal sampler in accordance with claim 1 in which the sampler is pre-evacuated.

5. A molten metal sampler comprising an outer evacuated housing having a continuous sidewall with an inside surface and first and second sidewall ends, said sidewall defining a housing interior, a sample mold having first and second ends, and a portion for forming a solidified sample said first sample mold end being the filling end, and mounting means for supporting said sample mold in said housing, said mounting means including a wall portion on said sample mold secured to said inside surface of said outer housing and including a projection portion which extends beyond the first end of said sample mold and a fusible cup connected to said first end of said outer housing, said cap having a recess to receive said mounting means projecting portion and wherein said mounting means projecting portion includes wall means for providing an evacuated annular receptacle to receive and solidify molten metal in an annular ring around said mounting means projecting portion to reinforce said outer housing to minimize erosion of said outer housing during immersion in a molten metal bath and wherein said wall means for providing an annular receptacle defines a tapered inlet having a diameter larger than the diameter of said sample mold and wherein said wall means providing an annular receptacle forms a knife edge for fusing with sample metal to seal gases evolving from said sample during cooling.

6. A molten metal sampler in accordance with claim 5 wherein said sample mold has a restricted portion intermediate the length to terminate the length of the sample being generated and an integral vacuum chamber extending remote from said restricted portion to afford increased vacuum reserve to assist in filling.

7. A molten metal sampler in accordance with claim 5 wherein said mounting means has a shoulder at the end of said taper and said sample mold first end is seated against said shoulder.

* * * * *